United States Patent
Nihongi et al.

(10) Patent No.: US 7,825,388 B2
(45) Date of Patent: Nov. 2, 2010

(54) CHARGED PARTICLE BEAM IRRADIATION SYSTEM AND CHARGED PARTICLE BEAM EXTRACTION METHOD

(75) Inventors: Hideaki Nihongi, Hitachi (JP); Koji Matsuda, Hitachi (JP); Kazuo Hiramoto, Hitachiohta (JP); Hiroshi Akiyama, Hitachiohta (JP)

(73) Assignee: Hitachi, Ltd., Tokyo (JP)

( * ) Notice: Subject to any disclaimer, the term of this patent is extended or adjusted under 35 U.S.C. 154(b) by 841 days.

(21) Appl. No.: 11/678,300

(22) Filed: Feb. 23, 2007

(65) Prior Publication Data
US 2008/0067405 A1    Mar. 20, 2008

(30) Foreign Application Priority Data
Feb. 24, 2006    (JP)    ............... 2006-047676

(51) Int. Cl.
H05H 9/00    (2006.01)
(52) U.S. Cl. ............ 250/492.3; 315/501; 607/2
(58) Field of Classification Search ............ 250/492.3; 315/501, 505, 507
See application file for complete search history.

(56) References Cited

U.S. PATENT DOCUMENTS

| | | | | |
|---|---|---|---|---|
| 5,256,454 | A * | 10/1993 | Murai et al. | 427/498 |
| 7,049,613 | B2 * | 5/2006 | Yanagisawa et al. | 250/492.3 |
| 7,154,107 | B2 * | 12/2006 | Yanagisawa et al. | 250/492.3 |
| 7,385,203 | B2 * | 6/2008 | Nakayama et al. | 250/400 |
| 7,394,082 | B2 * | 7/2008 | Fujimaki et al. | 250/492.3 |
| 7,456,415 | B2 * | 11/2008 | Yanagisawa et al. | 250/492.3 |
| 7,576,342 | B2 * | 8/2009 | Hiramoto et al. | 250/492.3 |
| 7,589,334 | B2 * | 9/2009 | Hiramoto et al. | 250/492.21 |
| 2005/0127306 | A1 * | 6/2005 | Yanagisawa et al. | 250/492.1 |
| 2005/0167616 | A1 * | 8/2005 | Yanagisawa et al. | 250/492.22 |
| 2006/0163496 | A1 * | 7/2006 | Hiramoto et al. | 250/492.3 |
| 2006/0226372 | A1 * | 10/2006 | Yanagisawa et al. | 250/396 R |

(Continued)

FOREIGN PATENT DOCUMENTS

JP    2006-239404    9/2006

OTHER PUBLICATIONS

W. I. Chu, et al., Rev. Sci. Instrum. 64(8), Aug. 1993, pp. 2055-2122.

*Primary Examiner*—Robert Kim
*Assistant Examiner*—Johnnie L Smith
(74) *Attorney, Agent, or Firm*—Mattingly & Malur, P.C.

(57) ABSTRACT

A charged particle beam irradiation system and a charged particle beam extraction method which can prevent erroneous irradiation of a charged particle beam in the direction of advance of the charged particle beam. The system and method are featured in stopping supply of an ion beam to one or more of a plurality of angle zones in each of which a target dose is attained, the angle zones being formed by dividing an RMW in a rotating direction thereof, and in allowing the supply of the ion beam to one or more other angle zones in each of which a target dose is not yet attained. The invention can easily adjust beam doses at various positions in an affected part of the patient body in the direction of advance of the ion beam, and can greatly reduce the probability of erroneous irradiation that the beam dose becomes excessive or deficient at the various positions within the affected part of the patient body in the direction of advance of the ion beam.

14 Claims, 11 Drawing Sheets

U.S. PATENT DOCUMENTS

2006/0273264 A1* 12/2006 Nakayama et al. ....... 250/492.3
2007/0051905 A1* 3/2007 Fujimaki et al. ......... 250/492.3
2007/0158592 A1* 7/2007 Hiramoto et al. ....... 250/492.21
2007/0228291 A1* 10/2007 Hiramoto et al. ......... 250/492.3
2007/0252093 A1* 11/2007 Fujimaki et al. ......... 250/492.3
2009/0283702 A1* 11/2009 Umezawa et al. ......... 250/492.3

* cited by examiner

FIG. 7

- INCIDENT ENERGY
- TYPE OF SECOND SCATTERER
- TYPE OF RANGE MODULATION WHEEL
- ROTATIONAL ANGLE OF GANTRY
- TYPE OF FIRST SCATTERER
- INSERTION AMOUNT OF RANGE SHIFTER
- ...

| ZONE NUMBER | START ANGLE [°] | END ANGLE [°] | TARGET VALUE | ALLOWABLE VALUE | RATIO ($N_i/N_s$) | ALLOWABLE VALUE | BEAM INTENSITY | ... |
|---|---|---|---|---|---|---|---|---|
| 1 | 0 | $\theta_1$ | $N_1$ | $\Delta N_1$ | $R_1$ | $\Delta R_1$ | $I_1$ | |
| 2 | $\theta_1$ | $\theta_2$ | $N_2$ | $\Delta N_2$ | $R_2$ | $\Delta R_2$ | $I_2$ | |
| 3 | $\theta_3$ | $\theta_3$ | $N_3$ | $\Delta N_3$ | $R_3$ | $\Delta R_3$ | $I_3$ | |
| ... | ... | ... | ... | ... | ... | ... | ... | |
| i | $\theta_{i-1}$ | $\theta_i$ | $N_i$ | $\Delta N_i$ | $R_i$ | $\Delta R_i$ | $I_i$ | |
| ... | ... | ... | ... | ... | ... | ... | ... | |
| N | $\theta_{N-1}$ | 360 | $N_N$ | $\Delta N_N$ | $R_N$ | $\Delta R_N$ | $I_N$ | |
| TOTAL | — | — | $N_s$ | $\Delta N_s$ | 1 | $\Delta R_s$ | — | |

FIG. 8

| ZONE NUMBER | START ANGLE [°] | END ANGLE [°] |
|---|---|---|
| 1 | 0 | $\theta_1$ |
| 2 | $\theta_1$ | $\theta_2$ |
| 3 | $\theta_3$ | $\theta_3$ |
| ... | ... | ... |
| i | $\theta_{i-1}$ | $\theta_i$ |
| ... | ... | ... |
| N | $\theta_{N-1}$ | 360 |

FIG. 9

| ZONE NUMBER | TARGET VALUE | ALLOWABLE VALUE | RATIO ($N_i/N_s$) | ALLOWABLE VALUE |
|---|---|---|---|---|
| 1 | $N_1$ | $\Delta N_1$ | $R_1$ | $\Delta R_1$ |
| 2 | $N_2$ | $\Delta N_2$ | $R_2$ | $\Delta R_2$ |
| 3 | $N_3$ | $\Delta N_3$ | $R_3$ | $\Delta R_3$ |
| ... | ... | ... | ... | ... |
| i | $N_i$ | $\Delta N_i$ | $R_i$ | $\Delta R_i$ |
| ... | ... | ... | ... | ... |
| N | $N_N$ | $\Delta N_N$ | $R_N$ | $\Delta R_N$ |
| TOTAL | $N_S$ | $\Delta N_S$ | 1 | $\Delta R_S$ |

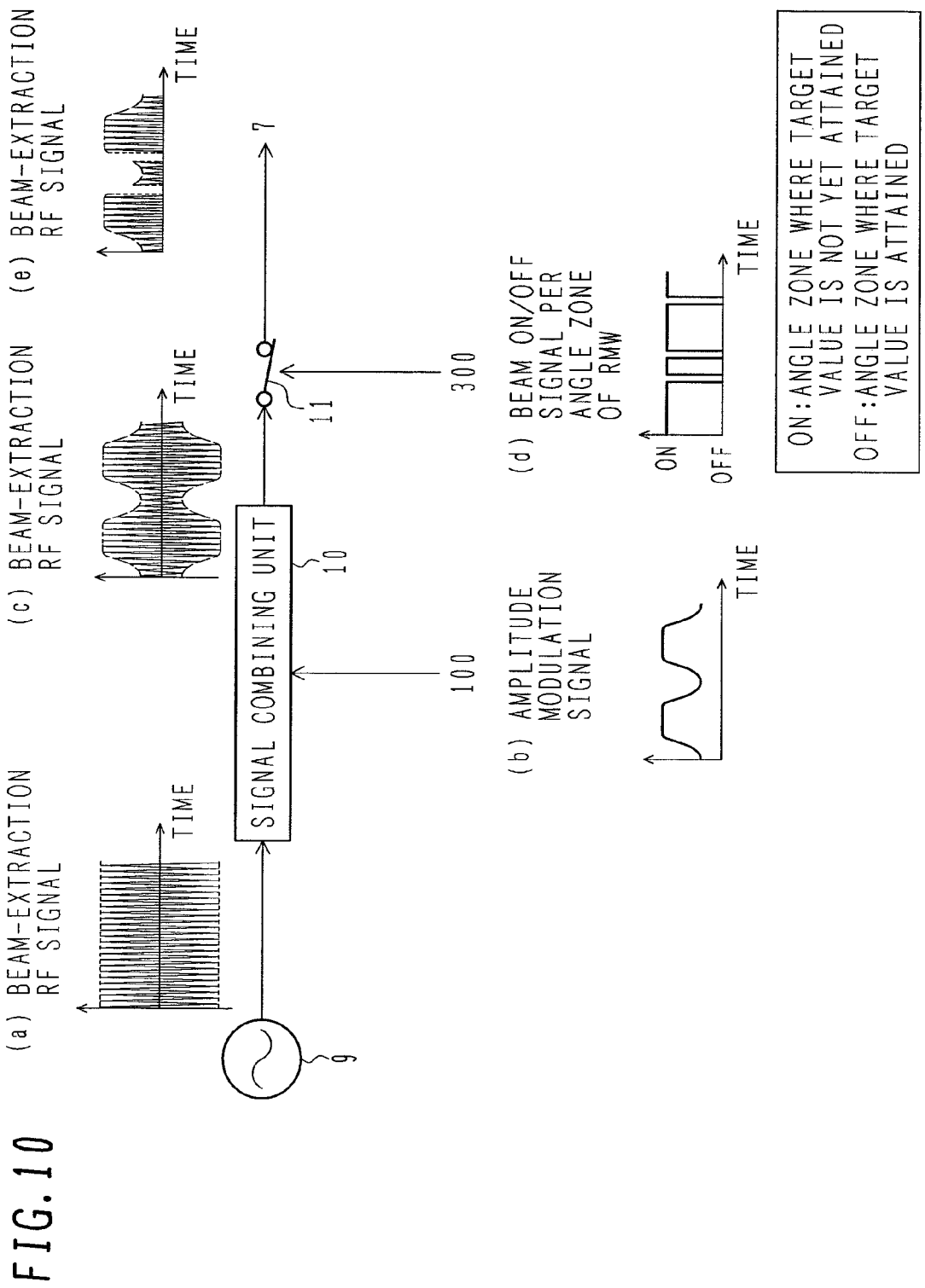

CHARGED PARTICLE BEAM IRRADIATION SYSTEM AND CHARGED PARTICLE BEAM EXTRACTION METHOD

BACKGROUND OF THE INVENTION

1. Field of the Invention

The present invention relates to a charged particle beam irradiation system and a charged particle beam extraction method. More particularly, the present invention relates to a charged particle beam irradiation system and a charged particle beam extraction method suitable for use as a particle beam therapy system in which an ion beam of, e.g., protons and carbon ions, is irradiated to an affected part in the body of a patient for treatment.

2. Description of the Related Art

There is known a therapy method for irradiating an ion beam (charged particle beam) of, e.g., protons or carbon ions, to an affected part of in the body of a patient, such as a cancer. An ion beam irradiation system for use in such therapy comprises a circular accelerator, a beam transport, and rotating irradiation equipment which includes an irradiation apparatus. The circular accelerator accelerates an ion beam circulating along an orbit to a target level of energy. The ion beam having been accelerated to the target level of energy is transported to the irradiation apparatus through the beam transport. The irradiation apparatus irradiates the ion beam after it has been formed in match with the shape of the affected part of the patient body. Known examples of the circular accelerator include means for circulating the ion beam along an orbit, means for bringing betatron oscillation of the ion beam into a resonant state outside the separatrix of resonance, and a synchrotron provided with a beam-extraction deflector for taking the ion beam out of the orbit.

The principle of the therapy using an ion beam is based on not only a characteristic that, immediately before the time when ions are stopped, most of energy of the ion beam is released and a dose distribution called a Bragg curve is formed, but also a characteristic that the position of the peak of the Bragg curve, i.e., the Bragg peak, in the direction of depth toward the inner side of the patient body from the body surface can be controlled depending on the magnitude of energy of the ion beam entering the patient body. By utilizing those characteristics, the energy of the ion beam is properly selected so that the ion beam is stopped near the affected part of the patient body and most of the ion beam energy is given to cancer cells of the affected part.

The Bragg peak has a width of several millimeters in the direction of depth (i.e., the direction of beam advance). Usually, the affected part has a thickness larger than the width of the Bragg peak in the direction of depth. In order to effectively irradiate the ion beam over the entire thickness of the affected part in the direction of depth, the energy of the ion beam (beam energy) and the dose of the ion beam must be controlled so as to form a wide and flat dose distribution corresponding to the size of the affected part.

From that point of view, in a known ion beam irradiation system, a range modulation wheel (hereinafter abbreviated to an "RMW") is installed in an irradiation apparatus (see, e.g., Non-Patent Document 1; "REVIEW OF SCIENTIFIC INSTRUMENTS" (August 1993; FIG. 30). The RMW has a structure having a plurality of energy absorbers (blades) in the form of wedges with an axial thickness changing step by step in the circumferential direction. The RMW is arranged to cross a beam path within the irradiation apparatus and is rotated in a plane perpendicular to the beam path. During the rotation of the RMW, when the ion beam passes through a thinner portion of the blade, the beam energy is less attenuated and the Bragg peak is produced at a deeper position inside the body. When the ion beam passes through a thicker portion of the blade, the beam energy is attenuated to a larger extent and the Bragg peak is produced at a shallower position nearer to the body surface. Further, the position of the Bragg peak varies cyclically with the rotation of the RMW. As a result, a wide and flat dose distribution (called Spread Out Bragg Peak: SOBP) can be obtained over a region from the shallow position near the body surface to the deep position inside the body, looking at the beam energy integrated over time.

SUMMARY OF THE INVENTION

The above-described known technique has the problem as follows.

Physical features, the size of the affected part, and the position of the affected part from the body surface differ depending on individual patients. Further, those items are also changed with the progress of treatment even for the same patient. Accordingly, a dose distribution optimum for the treatment differs depending on individual patients, the number of times of treatments made on the same patient, etc. However, because the RMW is structured such that the shape of the wedge-like energy absorber is optimized corresponding to the energy of the incoming ion beam, just one dose distribution is obtained with one RMW. For that reason, it is required to form and prepare a different RMW per size of the affected part in the patient body and to replace the RMW with another one optimum for another treatment whenever the size of the affected part is changed. Hence a difficulty has been experienced in smoothly carrying out treatments for a larger number of patients.

An object of the present invention is to provide a charged particle beam irradiation system and a charged particle beam extraction method which can reduce the probability of erroneous irradiation of a charged particle beam in the direction of advance of the charged particle beam.

To achieve the above object, according to one aspect, the present invention is featured in supplying a charged particle beam extracted from an accelerator to an energy adjusting device which is rotatable and has different axial thicknesses in a rotating direction thereof, and controlling start and stop of extraction of the charged particle beam from the accelerator in accordance with a rotational angle of the energy adjusting device and a dose of the charged particle beam having passed through the energy adjusting device.

According to another aspect, the present invention is featured in supplying a charged particle beam extracted from an accelerator to an energy adjusting device which is rotatable and has different axial thicknesses in a rotating direction thereof, stopping supply of the charged particle beam to one or more of a plurality of zones in each of which a target dose is attained, the zones being formed by dividing the energy adjusting device in the rotating direction, and allowing the supply of the charged particle beam to one or more other zones in each of which a target dose is not yet attained.

With the feature of the present invention of stopping the supply of the charged particle beam to one or more of the plurality of zones divided in the rotating direction in each of which the target dose is attained, and of allowing the supply of the charged particle beam to one or more other zones in each of which the target dose is not yet attained, beam doses can be easily adjusted at various positions within an irradiation target in the direction of advance of the charged particle beam. It is therefore possible to greatly reduce the probability of erroneous irradiation that the beam dose becomes excessive or deficient at various positions within the irradiation target in the direction of advance of the charged particle beam. Thus, a dose distribution within the irradiation target in the direction of advance of the charged particle beam can be easily adjusted to the desired one. Preferably, that probability can be reduced to zero.

According to the present invention, it is possible to greatly reduce the probability of erroneous irradiation that the beam dose becomes excessive or deficient at various positions within the irradiation target in the direction of advance of charged particles. As a result, a dose distribution within the irradiation target in the direction of advance of the charged particle beam can be easily adjusted to the desired one.

BRIEF DESCRIPTION OF THE DRAWINGS

FIG. 7 is a conceptual diagram showing a data table stored in a central controller memory which is one of components used in the present invention;

FIG. 8 is a conceptual diagram showing a data table stored in a zone determining unit memory which is one of components used in the present invention;

FIG. 9 is a conceptual diagram showing a data table stored in a target value memory which is one of components used in the present invention;

FIG. 10 shows the particle beam therapy system according to the one preferred embodiment of the present invention, and also shows RF signals for beam extraction;

DESCRIPTION OF THE PREFERRED EMBODIMENTS

One preferred embodiment of the present invention will be described in detail below with reference to the drawings.

Figure 1:
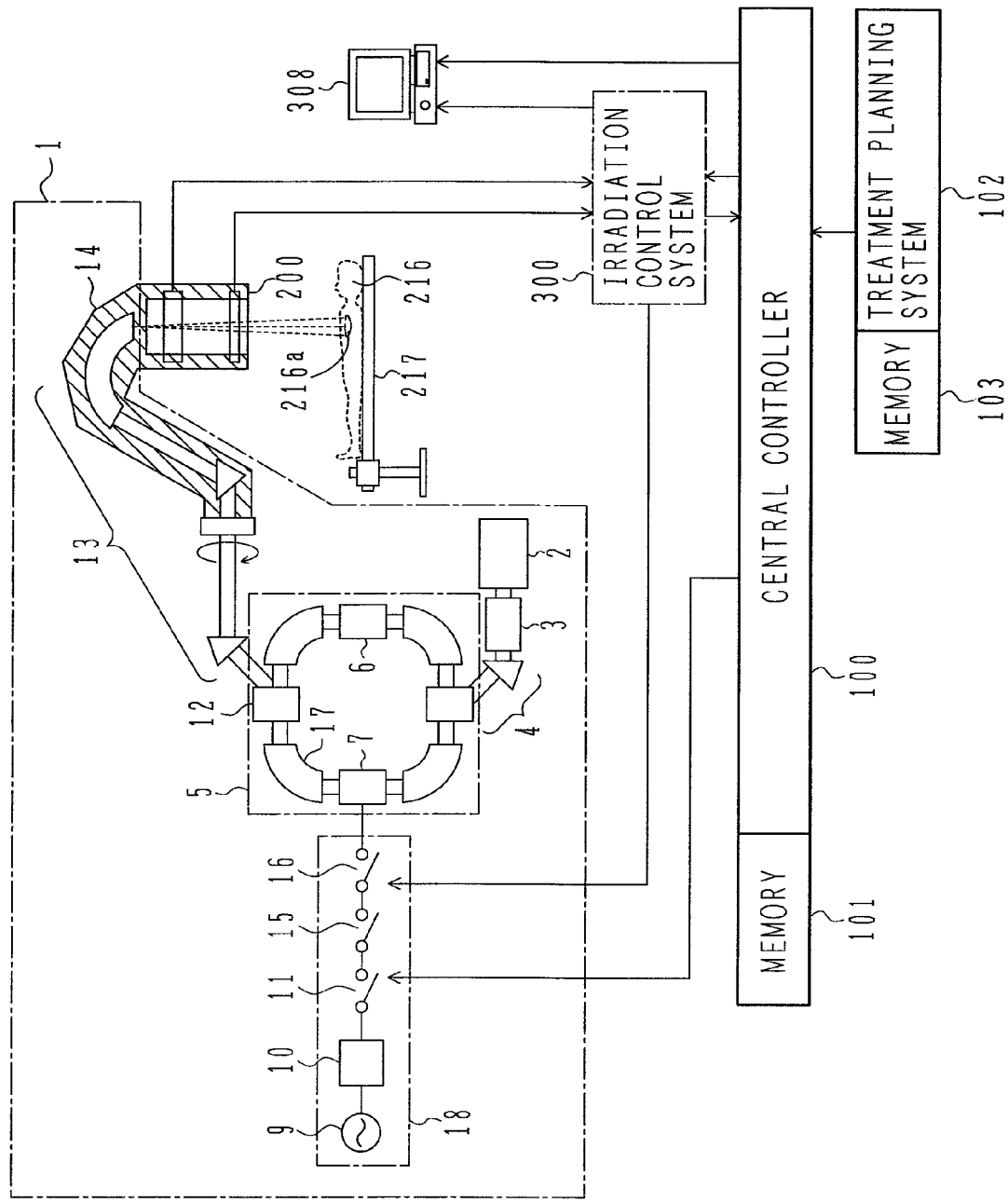
FIG. 1 is a conceptual diagram showing the overall construction of a particle beam therapy system (ion beam irradiation system) according to one preferred embodiment of the present invention.

As shown in FIG. 1, in a particle beam therapy system (ion beam irradiation system) according to this embodiment, an ion beam (e.g., a proton beam) is irradiated to an affected part 216a in the body of a patient 216 who is kept fixed on a treatment bed 217. The ion beam irradiation system comprises an ion beam generator (e.g., a proton beam generator or a particle beam generator) 1, a central controller 100, an irradiation apparatus 200, and an irradiation control system 300.

The central controller 100 reads irradiation conditions (such as the direction of beam irradiation, the SOBP width, the dose, the maximum irradiation depth, and the irradiation field size) which are decided in a treatment planning system 102 to form an irradiation field optimum for the affected part 216a in the body of the patient 216. Then, the central controller 100 selects operation parameters such as the device type, the installed position, the installation angle, the beam energy, the beam intensity pattern, and the target value of the beam dose (amount of the irradiated ion beam)). The central controller 100 includes a memory 101 and stores information, shown in FIG. 7, in the memory 101. Based on the information stored in the memory 101, each device is installed in the irradiation apparatus 200 and the operation parameters are set for the ion beam generator 1 and the irradiation control system 300.

The ion beam generator 1 is configured to generate an ion beam having a predetermined level of beam energy, and it comprises an ion source 2, a pre-accelerator 3, a low-energy beam transport 4, and a synchrotron 5.

The ion beam generated by the ion source 2 is pre-accelerated by the pre-accelerator 3 and is supplied to the synchrotron 5 through the low-energy beam transport 4.

The synchrotron 5 comprises, as shown in FIG. 1, an acceleration unit 6, an RF knockout unit 7 for beam extraction, a deflector 12 for beam extraction, quadruple magnets (not shown), and bending magnets 17, all of which are arranged along an orbit inside the synchrotron 5. The RF knockout unit 7 includes an RF knockout electrode (not shown) for beam extraction. The RF knockout unit 7 is connected to an RF supply unit 18 for beam extraction. The RF supply unit 18 comprises an RF power supply 9 for beam extraction, a signal combining unit 10, a beam ON/OFF switch (closing/opening device) 11, an extraction terminating switch 15, and an interlock switch 16. The RF power supply 9 is connected to the RF knockout electrode of the RF knockout unit 7 through the signal combining unit 10, the beam ON/OFF switch 11, the extraction terminating switch 15, and the interlock switch 16 in the order named. Thus, the RF knockout unit 7 is supplied with RF power from the RF power supply 9 through the interlock switch 16, the extraction terminating switch 15, and the beam ON/OFF switch 11, which are all closed, and through the signal combining unit 10. The ion beam circulating along the orbit inside the synchrotron 5 is accelerated by an RF wave applied to an RF cavity (not shown) disposed in the acceleration unit 6. After the ion beam is accelerated to have a desired level of energy (e.g., 50-250 MeV), the ion beam is extracted from the synchrotron 5 at the timing when the RF power from the RF power supply 9 is applied from the RF knockout electrode to the ion beam circulating inside the synchrotron 5.

A high-energy beam transport 13 interconnects the synchrotron 5 and the irradiation apparatus 200, and a part of the high-energy beam transport 13 is installed in a rotating gantry 14. The ion beam extracted from the synchrotron 5 is introduced through the high-energy beam transport 13 to the irradiation apparatus 200 which is installed in the rotating gantry 14. By adjusting a rotational angle of the rotating gantry 14, the ion beam can be irradiated to the patient 216 from the desired direction.

Figure 2:
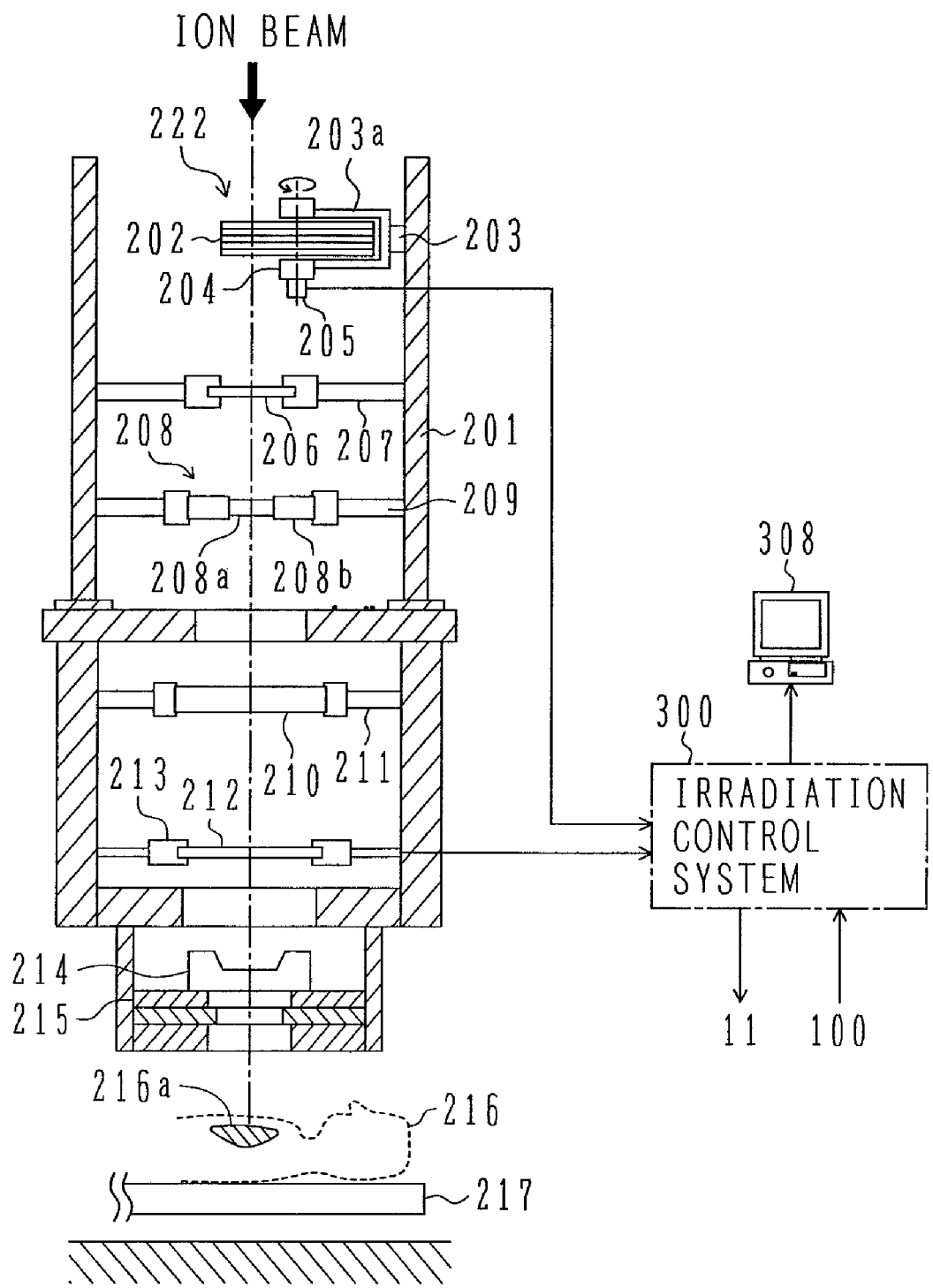
FIG. 2 is a conceptual diagram showing details of an irradiation apparatus installed in the particle beam therapy system according to the one preferred embodiment of the present invention.

The irradiation apparatus 200 will be described in detail below with reference to FIG. 2. The irradiation apparatus 200 serves as an apparatus for shaping the ion beam generated by the ion beam generator 1 in match with the shape of the affected part 216a in the body of the patient 216. The irradiation apparatus 200 includes a casing 201 which contains an RMW (range modulation wheel) 202 mounted to the casing 201 through an RMW holder 203, a first scatterer 206 mounted to the casing 201 through a first scatterer holder 207, a second scatterer 208 mounted to the casing 201 through a second scatterer holder 209, a range shifter 210 mounted to the casing 201 through a range shifter holder 211, a dose monitor 212 mounted to the casing 201 through a dose monitor holder 213, a bolus 214, and a collimator 215.

An RMW device 222 is an energy adjusting device which scans the Bragg peak with time and forms a wide and uniform dose distribution in the direction of depth of the affected part 216a. The RMW device 222 comprises the RMW 202, the RMW holder 203, and an RMW rotation driver 204. The RMW 202 is made of a material having a small beam scattering angle with respect to an energy loss (i.e., a material having a small atomic number, such as resin). The RMW holder 203 has a pair of holder arms 203a disposed in an opposed relation in the direction of a beam axis and is mounted to an inner wall of the casing 201. Rotating members (not shown) are rotatably mounted to the upper and lower holder arms 203a. The RMW 202 is interposed between the rotating members, and a rotary shaft 223 (FIG. 5) of the RMW 202 is coupled to the rotating members, whereby the RMW 202 is supported by the RMW holder 203. Because the RMW 202 is detachably mounted to the RMW holder 203, it is easily replaceable. The RMW holder 203 is disposed at a position not interfering with the beam path. The RMW rotation driver 204 is mounted to the lower holder arm 203a and is operated to rotate the RMW 202. An angle meter 205 is also disposed on the lower holder arm 203a. The angle meter 205 is connected to a zone determining unit 301 (FIG. 3) disposed in the irradiation control system 300. The angle meter 205 detects a rotational angle (rotational phase) of the RMW 202.

Figure 5:
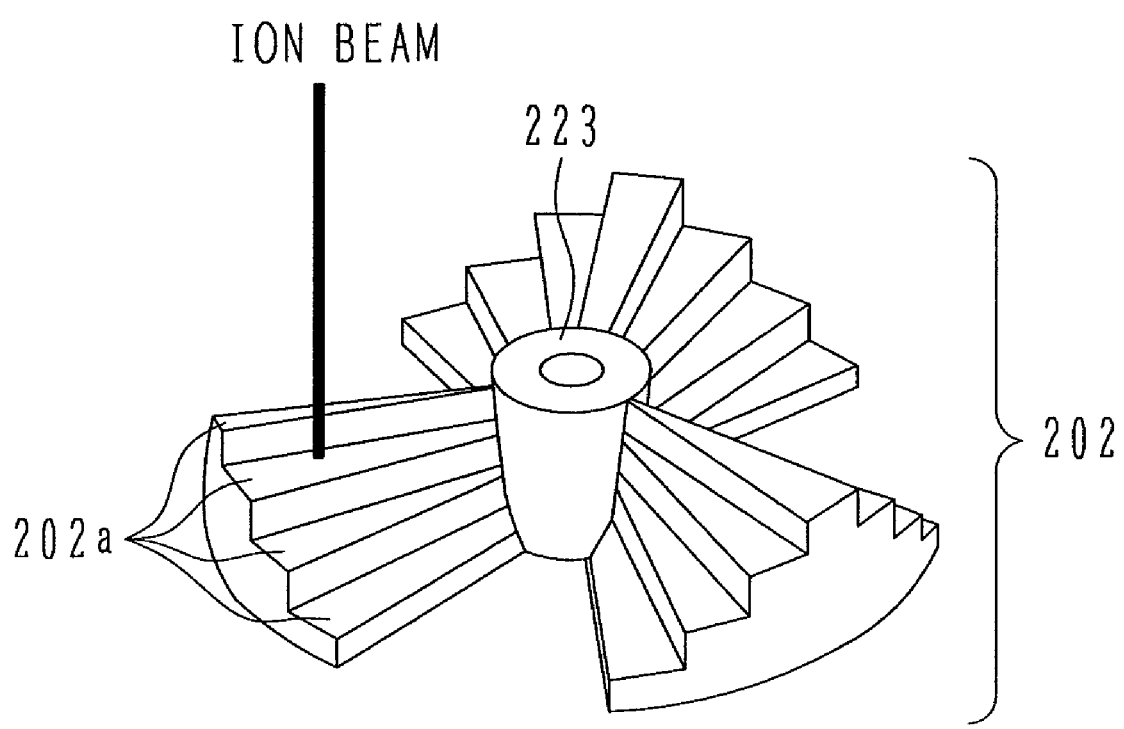
FIG. 5 is a perspective view showing the overall structure of a range modulation wheel.

A detailed structure of the RMW 202 is shown in FIG. 5. The RMW 202 has a rotary shaft 223 and a plurality (three in this embodiment) of blades 202a which are mounted to the rotary shaft 223 and are extended in the radial direction of the RMW 202. An opening is formed between adjacent two of the blades 202a in the circumferential direction of the RMW 202. There are three openings in one RMW 202. Each of the blades 202a has a plurality of plane areas arranged in the form of steps in the circumferential direction of the RMW 202, and each of the plane areas has a different thickness relative to a bottom surface of the RMW 202 in the axial direction. More specifically, each blade 202a is formed such that its thickness in the axial direction is increased in a stepwise way from each of the plane areas adjacent to the openings, which are positioned on both sides of the relevant blade 202a in the circumferential direction, toward the plane area positioned at a blade top portion having the largest thickness in the axial direction. In order to compensate for the difference in scattering rate of the ion beam caused by the difference in thickness from the blade bottom to each plane area, a scattering compensator may be attached to the RMW 202. With the rotation of the RMW 202 during the extraction of the ion beam, the thickness of a blade portion through which the ion beam passes is changed depending on the rotational angle of the RMW 202. Accordingly, the energy of the ion beam having passed through the RMW 202 is changed so as to form the Bragg peaks at different depths corresponding to respective levels of the beam energy. By thus scanning the Bragg peak with time, a flat irradiation field can be formed over a wide region at the desired depth in the affected part 216a. While the RMW 202 in this embodiment has the plurality of blades 202a each of which has a plurality of plane areas arranged in the form of steps in the rotating direction of the RMW 202, the structure of the RMW 202 is not limited to particular one so long as the axial thickness of the RMW 202 is changed in the rotating direction.

The first scatterer 206 has the function of spreading the ion beam in the direction perpendicular to the direction of advance of the ion beam (hereinafter referred to as the "perpendicular direction") based on an ion scattering phenomenon caused by a material of the first scatterer 206. The ion beam is spread into substantially the Gaussian distribution through the scattering. The first scatterer 206 is generally made of a material having a large atomic number, such as lead or tungsten, which has a small energy loss with respect to a scattering rate of the ion beam. The first scatterer 206 may be a mixture of plural materials or may be formed by stacking a plurality of plate members differing in thickness so that a total thickness of the first scatterer in the direction of advance of the ion beam is adjustably changed. While the first scatterer 206 is arranged downstream of the RMW 202 in the illustrated example, it may be arranged upstream of the RMW 202. Alternatively, the RMW 202 and the first scatterer 206 may be constituted as an integral unit. Further, in order to compensate for the difference in scattering rate of the ion beam caused by the difference in thickness of the blade 202a, a scattering compensator having a different thickness per certain angle may be attached to the RMW 202.

The second scatterer 208 has the function of forming a wide and uniform dose distribution from the ion beam which has been spread out by the first scatterer 206. The second scatterer 208 comprises a disk portion 208a and a ring portion 208b disposed around the disk portion 208a. The disk portion 208a is made of a material having a large beam scattering angle with respect to an energy loss during passage of the ion beam (i.e., a material having a large atomic number, such as lead or tungsten), and the ring portion 208b is made of a material having a small beam scattering angle with respect to an energy loss (i.e., a material having a small atomic number, such as resin). Also, the thicknesses of the disk portion 208a and the ring portion 208b are usually selected such that the amounts of energy losses of the ion beam entering both the portions are substantially equal to each other. Therefore, the ring portion 208b usually has a larger thickness than the disk portion 208a. When the ion beam having been spread out by the first scatterer 206 enters the disk portion 208a and the ring portion 208b, the ion beam having entered the disk portion 208a is spread out at a larger extent than that having entered the ring portion 208b, whereby a uniform distribution of the ion beam can be formed over a wide region in the perpendicular direction. Note that, instead of the above-described dual ring structure, the second scatterer 208 may have, for example, a structure including a larger number of rings or a structure in which the thickness of the second scatterer is moderately changed in the radial direction.

The range shifter 210 has the function of making a maximum range of the ion beam matched with the maximum depth of the affected part 216a. The range shifter 210 is made of a material having a small beam scattering angle with respect to an energy loss (i.e., a material having a small atomic number, such as resin). The maximum range of the ion beam can be reduced because the beam energy is lost when the ion beam passes through the range shifter 210. As a result, the maximum range of the ion beam can be made matched with the maximum depth of the affected part 216a. The range shifter 210 may be formed by stacking a plurality of plate members differing in thickness so that a total thickness of the range shifter in the direction of advance of the ion beam is adjustably changed depending on a combination of the plate members. Further, instead of using the range shifter 210, the maximum range of the ion beam may be adjusted by reducing the energy applied to accelerate the ion beam in the synchrotron 5, or by causing the energy of the ion beam to be consumed in the high-energy beam transport 13. Such a method is advantageous in cutting neutrons which are generated when the ion beam passes through the range shifter 210.

The ion beam having been spread out in both the perpendicular direction and the direction of depth through the above-described process enters the dose monitor 212 which measures the amount of the ion beam having passed through it. Arranging the dose monitor 212 in the downstream side in the direction of advance of the ion beam is advantageous in that the amount of the passing ion beam can be measured at a position immediately before irradiation to the affected part 216a. Arranging the dose monitor 212 in the upstream side, e.g., upstream of the device for changing the energy of the ion beam, such as the RMW 202 or the range shifter 210, is advantageous in eliminating the necessity of, e.g., correction calculations of an output signal from the dose monitor 212, which must be executed to compensate for the difference in energy of the ion beam.

The bolus 214 is formed by cutting a block made of resin, for example, into such a structure that the thickness of the resin block through which the ion beam passes is changed depending on the beam incident position in the lateral direction. With that structure, the energy of the ion beam having passed through the bolus 214 can be changed for each of the incident positions so that the penetration depth of the ion beam is matched with the shape of the affected part 216a in the direction of depth.

The collimator 215 is made of a radiation shield material and has a penetration hole formed corresponding to the affected part 216a. On a part of the ion beam spread out in the perpendicular direction, which passes through the penetration hole, is irradiated to the affected part 216a.

The bolus 214 and the collimator 215 are usually machined in match with the shape of the affected part 216a, and they are replaced for each affected part 216a. A multi-leaf collimator may be used as the collimator 215. By moving leaves to be matched with the shape of the affected part 216a in the lateral direction, time and labor required for machining and replacing the collimator can be omitted.

Figure 3:
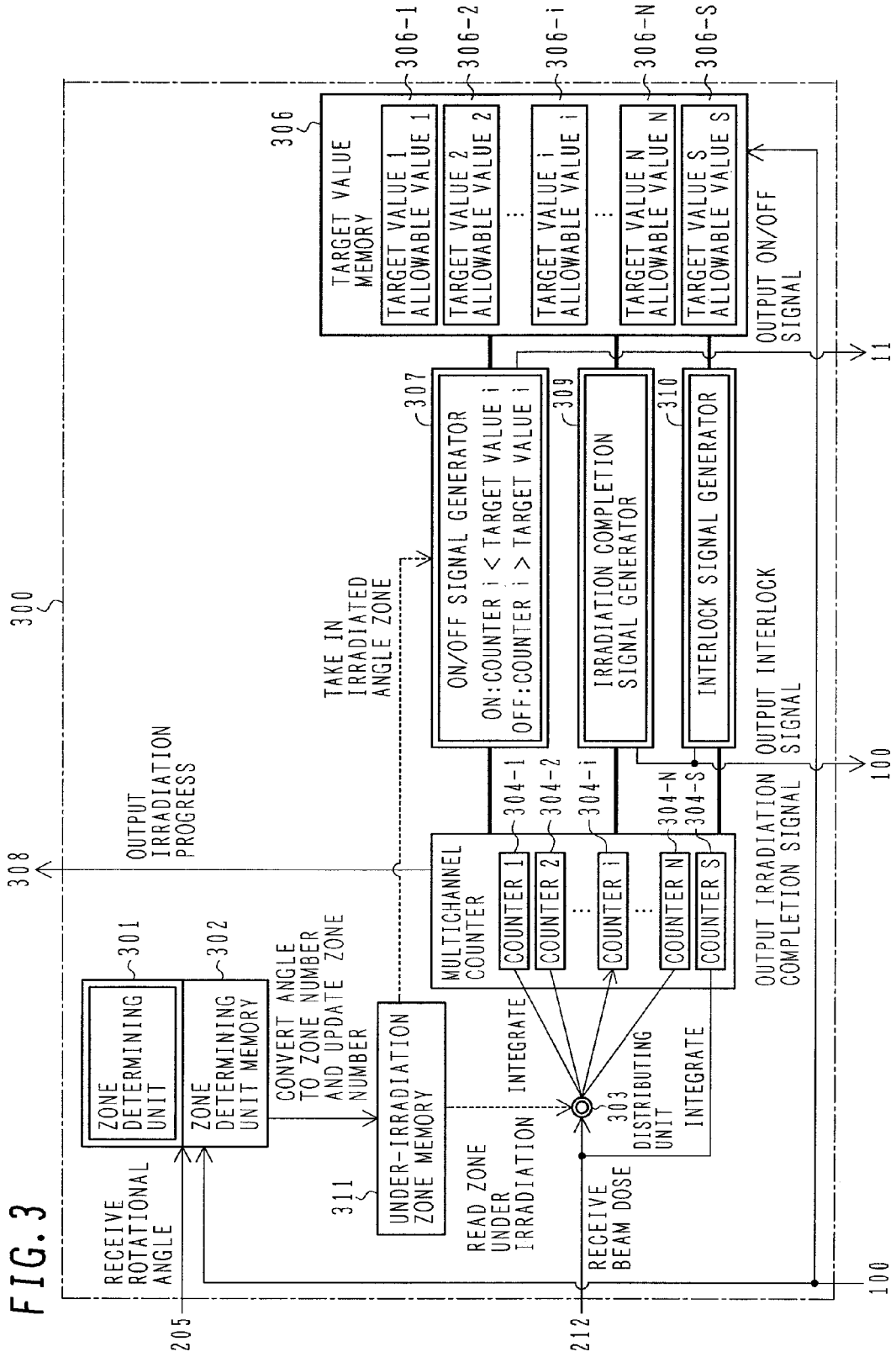
FIG. 3 is a conceptual diagram showing the construction of an irradiation control system installed in the particle beam therapy system according to the one preferred embodiment of the present invention.

Details of the irradiation control system 300 will be described below with reference to FIG. 3.

The irradiation control system 300 manages the amount of the passing ion beam (beam dose) per angle zone of the RMW 202 in order to form the desired irradiation field. The term "angle zone" means one of plural zones obtained by dividing the RMW 202 in the circumferential direction. In other words, the RMW 202 forms a plurality of angle zones (in practice, a large number of angle zones) in the circumferential direction. The irradiation control system 300 comprises a zone determining unit 301, a distributing unit 303, an ON/OFF signal generator 307, an irradiation completion signal generator 309, an interlock signal generator 310, a memory (target value memory) 306, a counter (e.g., a multi-channel counter) 304, and a memory (under-irradiation zone memory) 311.

The zone determining unit 301 includes a memory (zone determining unit memory) 302. The zone determining unit 301 is connected to the central controller 100, the angle meter 205, and the memory 311.

The distributing unit 303 is connected to the memory 311, the dose monitor 212, and the counter 304. The ON/OFF signal generator 307 is connected to the memory 311, the counter 304, the memory 306, and the beam ON/OFF switch 11. The irradiation completion signal generator 309 is connected to the counter 304, the memory 306, and the central controller 100. The interlock signal generator 310 is connected to the counter 304, the memory 306, and the central controller 100. The counter 304 includes a total of (N+1) counters, i.e., a number N of counters from Counter 1 (304-1) to Counter N (304-N) and Counter S (304-S). The number N of counters (from the counter 304-1 to the counter 304-N) are connected to the dose monitor 212 through the distributing unit 303. The counter 304-S is connected to the dose monitor 212 while bypassing the distributing unit 303.

Figure 4:
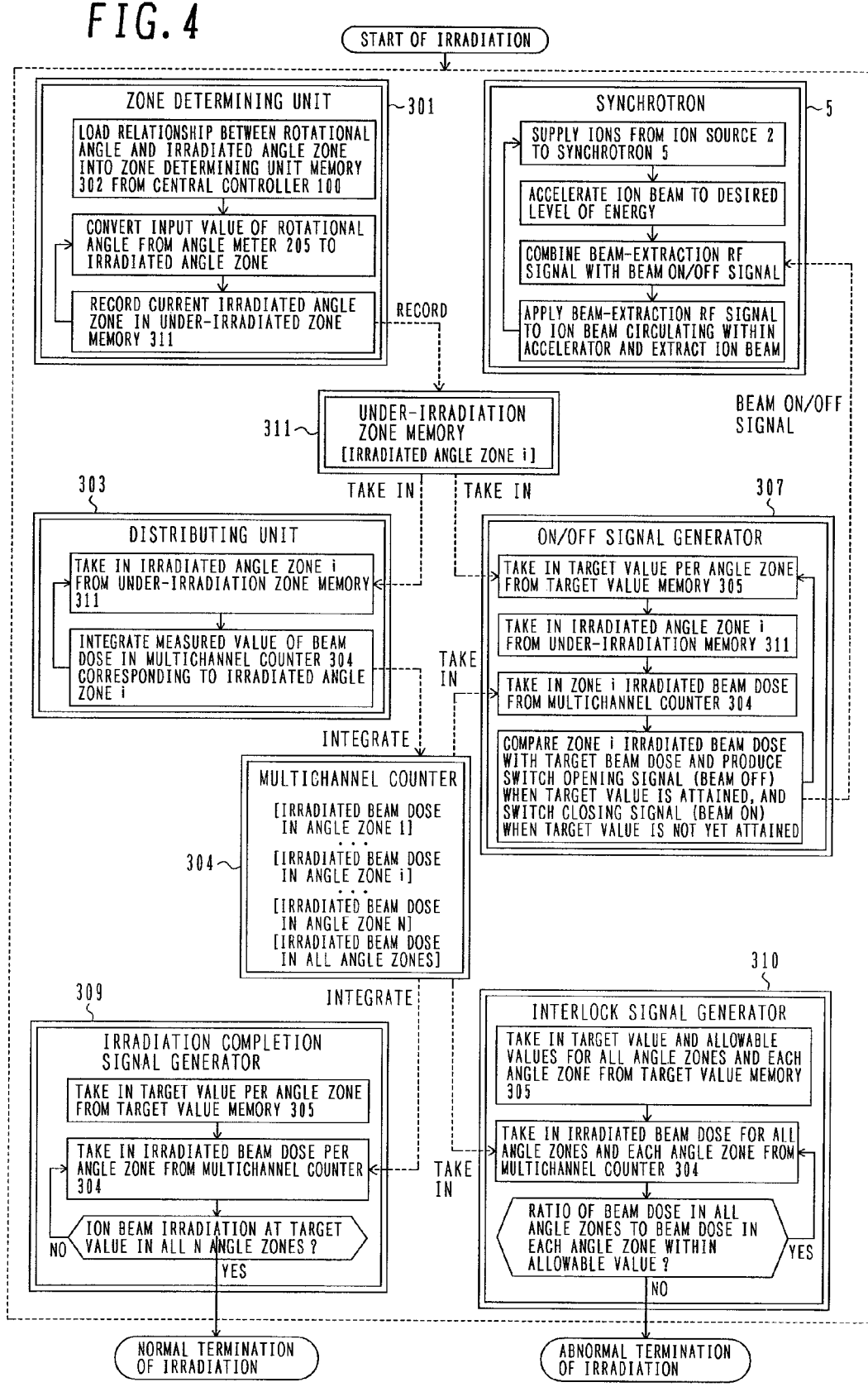
FIG. 4 is a flowchart showing control procedures executed for beam irradiation to form an irradiation field in the particle beam therapy system according to the one preferred embodiment of the present invention.

With reference to FIG. 4, the following description is made of individual functions of the components of this embodiment and correlations among them primarily in relation to the irradiation control system 300.

When a beam irradiation start signal is generated by the central controller 100, the synchrotron 5, the zone determining unit 301, the distributing unit 303, the ON/OFF signal generator 307, the irradiation completion signal generator 309, and the interlock signal generator 310 start operations, and the extraction of the ion beam from the synchrotron 5 is started.

First, those items among information stored in the memory 101 of the central controller 100, which are shown in FIG. 9, i.e., a target beam dose (target value), its allowable value (allowable difference), a ratio (Ni/Ns) of the target beam dose, and its allowable value per angle zone, are loaded into the memory 306 of the irradiation control system 300. Those items of related information (such as the target beam dose (target value) and its allowable value, etc.) corresponding to zone numbers are stored respectively in memory areas 306-1, 306-2, . . . , 306-i, . . . , 306-N and 306-S within the memory 306.

The zone determining unit 301 has the function of converting the rotational angle measured by the angle meter 205 to the irradiation angle zone. In the zone determining unit memory 302, selected rotational angles of the RMW 202 and the angle zones (assuming a total number of angle zones to be N) corresponding to those selected rotational angles are registered in the form of a data table containing correlated information (FIG. 8) with regards to the number of the angle zone (hereinafter referred to as the "zone number"), the start angle of each angle zone, and the end angle of each angle zone. Those items of information are taken in by the zone determining unit 301 from the memory 101 of the central controller 100.

As shown in FIG. 7, the memory 101 of the central controller 100 stores the zone number, the start angle, the end angle, the target value, the allowable value of the target value, the ratio, the allowable value of the ratio, the beam intensity, etc. The start angle and the end angle are values decided depending on the type of the RMW 202. In other words, the zone number, the start angle, and the end angle represent rotational angle information of the RMW 202 per angle zone. More specifically, the angle zone having the zone number 1 is a zone where the rotational angle of the RMW 202 ranges from $\theta_{i-1}$ to $\theta_i$, and the angle zone having the zone number i is a zone where the rotational angle of the RMW 202 ranges from $\theta_{i-1}$ to $\theta_i$. FIG. 7 shows, by way of example, the data table containing one set of data covering the rotational angle from 0° to 360°. However, if the thickness of the RMW 202 is cyclically changed, the data table may contain one set of data corresponding to one cycle. The term "target value" represents the target value of the beam dose. In other words, it means the target value of the beam dose for each zone number of the RMW 202 selected for the relevant patient. The term "allowable value of the target value" represents the allowable value of the target value of the beam dose for each zone number of the RMW 202. The term "ratio" represents the ratio of the beam dose in each angle zone to the total beam dose. The term "allowable value of the ratio" represents the allowable value of the ratio.

The information shown in FIG. 7 and stored in the memory 101 is information prepared by a doctor using the treatment planning system 102 in the stage of treatment planning for the relevant patient. The thus-prepared information, shown in FIG. 7, is temporarily stored in the memory 103 and loaded into the memory 101 by the central controller 100 prior to the treatment of the relevant patient.

Then, during the irradiation of the ion beam to the affected part 216a, the zone determining unit 301 converts the rotational angle of the RMW 202, which is inputted from the angle meter 205, to the angle zone through which the ion beam is passing at that time, specifically the zone number (assumed to be i) of the relevant angle zone, by using the above-described data table. The relevant angle zone of that zone number (i.e., the angle zone through which the ion beam is passing at that time) is called here the irradiated angle zone. The irradiated angle zone is stored in the memory (under-irradiation zone memory) 311. Thus, the angle zone positioned in the beam path within the irradiation apparatus 200 (i.e., the irradiated angle zone) is stored in the memory 311. The process of converting the rotational angle of the RMW 202, which is measured by the angle meter 205, to the irradiated angle zone and storing the irradiated angle zone in the memory 311, is repeatedly executed during the extraction of the ion beam. Consequently, the irradiated angle zone positioned in the beam path is always stored in the memory 311.

The penetration depth of the ion beam within the body of the patient 216 is decided depending on the thickness of the RMW 202 in the axial direction. By making the angle zone and the thickness of the RMW 202 in the axial direction in the relevant angle zone properly matched with each other, therefore, the ion beam dose can be managed with respect to the penetration depth of the ion beam. However, the match therebetween is not necessarily required. The information stored in the memory (zone determining unit memory) 302 is prepared, as shown in FIG. 8, in the form of a data table containing one set of data covering the rotational angle from 0° to 360°. However, if the thickness of the RMW 202 is cyclically changed, the data table may contain one set of data corresponding to one cycle. Note that the information shown in FIG. 8 is a part of the information shown in FIG. 7.

The distributing unit 303 has the function of distributing the beam dose (i.e., the amount of the passing ion beam), which is successively measured by the dose meter 212, to the respective counters in the counter 304 which correspond to the angle zones of the RMW 202. First, the distributing unit 303 reads the irradiated angle zone (zone number i) stored in the memory 311. Then, the distributing unit 303 outputs the beam dose obtained from the dose monitor 212 to the counter 304-i corresponding to the read zone number i. In other words, the beam dose (amount of the irradiated ion beam) measured for the irradiated angle zone of the zone number i is recorded in the counter 304-i in an integrated manner. Simultaneously, a signal indicating the beam dose, which is measured by the dose meter 212, is also outputted to the counter 304-S while bypassing the distributing unit 303. Thus, the beam doses in all the irradiated angle zones (of the zone numbers 1 to N) can be counted independently of each other. The total beam dose may be obtained by totalizing the respective count values of the counter 304-1 to the counter 304-N. By obtaining the total beam dose in such a way, the counter 304-S can be dispensed with. Further, a method of recording the beam doses in the respective counters may be executed through the steps of inputting the signal of the beam dose to all the counters from the counter 304-1 to 304-N at all times, and switching on/off counting of the counter 304 such that when the irradiated angle zone i is determined, the counting of only the corresponding counter 304-i is turned on, while the counting of the other counters is turned off.

The ON/OFF signal generator 307 has the function of comparing the irradiated beam dose with the target beam dose (hereinafter referred to as the "target value") for the angle zone positioned in the beam path within the irradiation apparatus 200 (i.e., the irradiated angle zone), and of opening and closing the beam ON/OFF switch 11, to thereby execute ON/OFF control of the beam extraction from the synchrotron 5. First, the ON/OFF signal generator 307 takes in the target value per angle zone from the memory 306. Then, the ON/OFF signal generator 307 takes in the zone number of the irradiated angle zone i from the memory 311 and compares the taken-in target value and the irradiated beam dose in the relevant irradiated angle zone with each other. If the irradiated beam dose reaches the target value, the ON/OFF signal generator 307 generates a beam OFF signal and transfers the beam OFF signal to the beam ON/OFF switch 11. Responsively, the beam ON/OFF switch 11 is opened to stop the application of the RF signal for beam extraction to the RF knockout unit 7 in the irradiated angle zone i. As a result, the extraction of the ion beam from the synchrotron 5 is stopped. If the irradiated beam dose is less than the target value, the ON/OFF signal generator 307 generates a beam ON signal and transfers the beam ON signal to the beam ON/OFF switch 11. The beam ON/OFF switch 11 is closed by the beam ON signal to allow the application of the RF signal for beam extraction to the RF knockout unit 7. As a result, the ion beam is irradiated to only the angle zone where the irradiated beam dose is less than the target value.

In stead of providing the memory 311 as described above, the result of the determination by the zone determining unit 301 as to the beam-irradiated angle zone may be directly inputted to the distributing unit 303 and the ON/OFF signal generator 307. With that modification, however, the control becomes more complicated because of the necessity of making the timing of the inputting of the determination result matched with the operation of the zone determining unit 301 so that the information of the irradiated angle zone positioned in the beam path is properly inputted to the distributing unit 303 and the ON/OFF signal generator 307.

With the progress of the irradiation of the ion beam, the ion beam is irradiated to the affected part 216a through each angle zone in amount corresponding to the target value. During the irradiation process, it happens sometimes that the ion beam is irradiated to the affected part 216a in a deviated state due to noise or other causes. The interlock signal generator 310 has the function of preventing the patient 216 from being subjected to excess irradiation of the ion beam against an unlikely event. For that purpose, the interlock signal generator 310 first takes in, from the memory 306, the target value and its allowable value per angle zone, as well as the target value and its allowable value for all the angle zones. Prior to that step, the memory 306 has already taken in, in addition to the target value per angle zone loaded from the central controller 100 as described above, the beam target dose value for all the angle zones, and the allowable values for each angle zone and all the angle zones. Then, the interlock signal generator 310 takes in the irradiated beam dose for each angle zone and all the angle zones from the counter 304. The counter 304-S counts the total dose of the ion beam. By taking a count ratio of the counter 304-i to the counter 304-S, therefore, a ratio of the dose of the ion beam irradiated to the angle zone of the zone number i to that irradiated to all the angle zones can be calculated. A determination is made on whether the count value of the counter 304-S (i.e., the dose of the ion beam irradiated to all the angle zones) is less than the sum of (the target value S+ the allowable value S). If the count value exceeds the sum of (the target value S+ the allowable value S), this means excess irradiation of the ion beam. Therefore, the interlock signal generator 310 generates a beam irradiation stop signal and transfers the beam irradiation stop signal to the central controller 100. A similar operation is also executed for each angle zone. More specifically, a determination is made on whether the ratio of the beam dose in each angle zone to the total dose in all the angle zones, which are obtained from the counter 304, is within the target ratio ($R_i \pm \Delta R_i$). If the calculated ratio exceeds the allowable ratio, this means a deviation of the beam dose among the individual angle zones. In that case, therefore, the interlock signal generator 310 also generates a beam irradiation stop signal and transfers the beam irradiation stop signal to the central controller 100. Upon receiving the beam irradiation stop signal, generates a beam extraction stop command and outputs the beam extraction stop command to the interlock switch 16 through a signal line (not shown). Responsively, the interlock switch 16 is opened to stop the supply of the RF power from the RF power supply 9 to the RF knockout electrode. As a result, the extraction of the ion beam from the synchrotron 5 is stopped. By thus repeatedly taking in the current beam dose from the counter 304 and confirming that the beam dose itself and the beam dose ratio are held within the allowable ranges, it is possible to prevent unexpected erroneous irradiation of the ion beam.

The irradiation completion signal generator 309 has the function of determining whether the ion beam has been irradiated in target amounts in all the angle zones, and generating an irradiation completion signal if so. Prior to the start of the irradiation, the irradiation completion signal generator 309 takes in the target value per angle zone from the target value memory 306. During the irradiation, the irradiation completion signal generator 309 takes in the irradiated beam dose per angle zone from the counter 304. It then compares the target value with the irradiated beam dose per angle zone. If the irradiated beam doses reach the target values in all the angle zones, the irradiation completion signal generator 309 outputs the irradiation completion signal to the central controller 100. If there is still even at least one angle zone where the beam dose is less than the target value, the irradiation completion signal generator 309 executes again the above-described process of taking in the irradiated beam dose from the counter 304 and comparing it with the target value. Because the ion beam is successively irradiated with the function of the ON/OFF signal generator 307 to only the angle zone where the beam dose is less than the target value, the beam dose of the target value is eventually irradiated in all the angle zones. Upon receiving the irradiation completion signal, the central controller 100 generates a beam extraction terminating signal and transfers the generated signal to the extraction terminating switch 15. In response to the beam extraction terminating signal, the extraction terminating switch 15 is opened to stop the supply of the RF power to the RF knockout electrode. As a result, the extraction of the ion beam from the synchrotron 5 is stopped.

The display 308 displays the beam dose and the target value per angle zone of the RMW 202. More specifically, the display 308 is connected to the counter 304 and the central controller 100, and it successively displays the dose counter value (measured by the dose monitor 212) per angle zone, the dose counter value in all the angle zones, and the target value per angle zone during the beam irradiation, thereby informing the progress of the beam irradiation to an operator. Also, the display 308 displays irradiation parameters and the devices used at that time so that the operator can easily recognize the beam irradiation conditions. Further, the display 308 may display the ratio of the beam dose per angle zone to the total beam dose as well. Looking at the displayed ratio, the operator can recognize that the irradiation is progressed without deviation.

Treatment of the affected part 216a, e.g., a cancer, using the particle beam therapy system of this embodiment will be described below. The ion beam generated from the ion source 2 is accelerated by the pre-accelerator 3 and is supplied to the synchrotron 5 through the low-energy beam transport 4. While circulating inside the synchrotron 5, the ion beam is accelerated by the RF cavity (not shown). After the ion beam is accelerated to have a desired level of energy, the RF power from the RF power supply 9 is applied to the ion beam circulating inside the synchrotron 5 from the RF knockout electrode through the beam ON/OFF switch 11, the extraction terminating switch 15, and the interlock switch 16 which are all closed. Correspondingly, the ion beam circulating within the separatix of resonance is caused to transit to the outside of the separatix, whereby the ion beam is extracted from the synchrotron 5. The extracted ion beam is introduced to the irradiation apparatus 200 through the beam-extraction deflector 12 and the beam transport 13. In the irradiation apparatus 200, the ion beam passes through the RMW 202, the first scatterer 206, the second scatterer 208, the range shifter 210, the dose monitor 212, the bolus 214, and the collimator 215 which are all arranged on the beam path. Thereafter, the ion beam is irradiated to the affected part 216a in the body of the patient 216 lying on the treatment bed 217. During the irradiation, the RMW 202 is continuously rotated.

The amount of the ion beam irradiated after passing through the irradiation apparatus 200 (i.e., the beam dose) is measured by the dose monitor 212. When the beam dose measured by the dose monitor 212 reaches the target dose value, the extraction terminating switch 15 is opened to stop the extraction of the ion beam from the synchrotron 5. As a result, the irradiation of the ion beam to the patient 216 is terminated.

In this embodiment, to adjust uniformity of the dose distribution in the direction of advance of the ion beam (i.e., in the direction of depth) within the affected part 216a, the amount of the ion beam extracted from the synchrotron 5 is controlled in accordance with a desired modulation signal pattern during the extraction of the ion beam so that the amount of the extracted ion beam is changed depending on the rotational angle of the RMW 202. A method of controlling the extraction of the ion beam in accordance with a desired intensity pattern from the synchrotron 5 will be described in detail below with reference to FIG. 10.

The irradiation control system 300 includes an extracted beam amount controller (not shown). The extracted beam amount controller has two functions. The first function is to form the SOBP width corresponding to the affected part 216a. More specifically, the extracted beam amount controller produces a beam ON/OFF signal (d) in FIG. 10 which closes the beam ON/OFF switch 11 when the rotational angle of the RMW 202 measured by the angle meter 205 reaches the rotational angle at which the extraction of the ion beam is to be started, and which opens the beam ON/OFF switch 11 when the measured rotational angle reaches the rotational angle at which the extraction of the ion beam is to be stopped. The SOBP width generated inside the patient body by the irradiation of the ion beam is adjusted in accordance with such on/off control of the beam ON/OFF signal (d). The second function of the extracted beam amount controller is to adjust the amount of the ion beam extracted from the accelerator (e.g., the synchrotron 5). More specifically, the extracted beam amount controller produces an amplitude modulation signal (b) corresponding to the magnitude of the target value per angle zone based on both the rotational angle of the RMW 202 measured by the angle meter 205 and preset intensity pattern data, thus adjusting the amount of the ion beam extracted from the accelerator in accordance with the amplitude modulation signal (b). The RF power supply 9 outputs an RF signal (a), which is generated by itself for the beam extraction, to the signal combining unit 10. The signal combining unit 10 combines the RF signal (a) and the amplitude modulation signal (b) with each other, to thereby produce a beam-extraction RF signal (c). The beam-extraction RF signal (c) is outputted to the beam ON/OFF switch 11. The beam ON/OFF switch 11 is connected to the extracted beam amount controller in the irradiation control system 300 and is closed and opened in response to the beam ON/OFF signal (d) produced by the extracted beam amount controller. With that switching operation, a beam-extraction RF signal (e) is supplied to the RF knockout electrode of the RF knockout unit 7 through the beam ON/OFF switch 11 and is applied to the ion beam circulating inside the synchrotron 5. When the beam ON/OFF switch 11 is closed, the ion beam is extracted from the synchrotron 5, and when the beam ON/OFF switch 11 is opened, the extraction of the ion beam from the synchrotron 5 is stopped. In that process, the interlock switch 16 and the extraction terminating switch 15 are kept closed. During a period in which the beam ON/OFF switch 11 is closed, i.e., in which the ion beam is extracted from the synchrotron 5, the amount of the ion beam extracted from the synchrotron 5 is adjusted in accordance with the beam-extraction RF signal (e). The larger the amplitude of the amplitude modulation signal (b), the larger is the amount of the ion beam extracted from the synchrotron 5. Conversely, the smaller the amplitude of the amplitude modulation signal (b), the smaller is the amount of the ion beam extracted from the synchrotron 5.

Because a plurality of SOBP widths can be formed by one RMW 202 with the above-described first function, the number of the RMWs 202 to be prepared can be reduced. Also, because the above-described second function enables one RMW 202 to be adapted for the ion beam having a wider energy range, the number of the RMWs 202 to be prepared can be further reduced. Moreover, with the second function, it is possible to adjust the amount of the extracted ion beam and hence to easily form a desired dose distribution within the affected part 216a in the direction of advance of the ion beam. The advantage obtained with the second function will be described in more detail below. It is assumed here that, when one RMW 202 suitable for a certain level of energy is used, the desired dose distribution within the affected part 216a in the direction of advance of the ion beam is as per indicated by a solid line in FIG. 11. Also, it is assumed that, when the energy of the ion beam to be introduced to one RMW 202 is increased and supplied to the one RMW 202 without using the above-described extracted beam amount controller, a mismatched dose distribution is obtained as per indicated by a dotted line in FIG. 11. Even in such a case, the desired dose distribution indicated by the solid line in FIG. 11 can be obtained by adjusting the amount of the extracted ion beam with the extracted beam amount controller according to this embodiment. Conversely, even when the dose distribution indicated by the dotted line in FIG. 11 is the desired one and the ion beams having different levels of energy are irradiated to the affected part, such a desired dose distribution can also be obtained by adjusting the amount of the extracted ion beam with the extracted beam amount controller.

Figure 6:
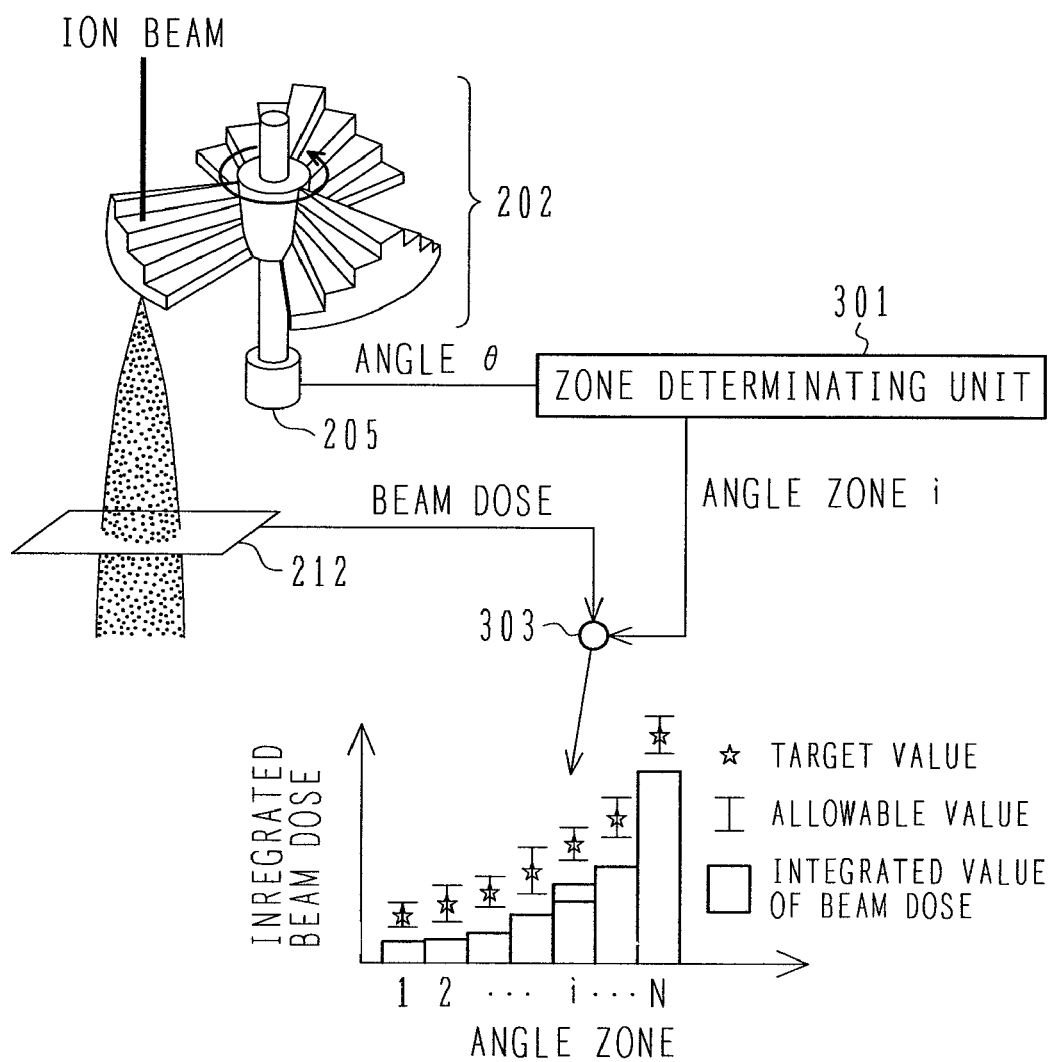
FIG. 6 is an illustration for explaining dose management per blade of the range modulation wheel, which is executed in an irradiation controller.

The operation of the ON/OFF signal generator 307 will be described in more detail below with reference to FIG. 6. As described above, the zone determining unit 301 determines, based on the above-mentioned data table, the zone number of the angle zone, which is positioned in the beam path at that time, from the rotational angle of the RMW 202 measured by the angle meter 205. The distributing unit 303 distributes, based on the determined zone number (i.e., the irradiated angle zone), the beam dose (i.e., the amount of the irradiated ion beam), which is successively measured by the dose monitor 212, to the counter included in the counter 304 and corresponding to the relevant irradiated angle zone (i.e., one of the counters 304-1 to 304-N). With that operation of the distributing unit 303, the irradiated beam doses are integrated in the counters 304-1 to 304-N (see a graph at the bottom of FIG. 6). For each of the angle zones, the target value of the beam dose (i.e., the target dose value) and its allowable value are set as described above. The axial thickness of the RMW 202 in the angle zone of the zone number N represents the thinnest one of the circumferentially divided angle zones of the RMW 202 through which the ion beam passes along the beam path during the period from the start of the extraction of the ion beam to the stop of the extraction. The target value of the beam dose for the angle zone of the zone number N is maximum. Also, the axial thickness of the RMW 202 in the angle zone of the zone number 1 represents the thickest one of the circumferentially divided angle zones of the RMW 202 through which the ion beam passes along the beam path during the period from the start of the extraction of the ion beam to the stop of the extraction. In most cases, the target value of the beam dose for the angle zone of the zone number 1 is minimum. The ion beam passing through the angle zone of the zone number N reaches the deepest position within the affected part 216a in the direction of advance of the ion beam. The ion beam passing through the angle zone having a smaller zone number reaches a shallower position in the direction of advance of the ion beam. In the affected part 216a, the ion beam irradiated to a deeper position acts to increase the dose at the shallower position to some extent. For that reason, the target value of the beam dose (target dose value) for the ion beam irradiated to the shallower position in the affected part 216a is set to be smaller than that for the ion beam irradiated to the deeper position. In other words, a smaller target value is set for the angle zone having a smaller zone number.

Per angle zone corresponding to each zone number, the ON/OFF signal generator 307 determines the integrated value of the amount of the irradiated ion beam (i.e., the integrated dose value), which is measured by the dose monitor 212, reaches the target value. The ON/OFF signal generator 307 generates the beam OFF signal for the angle zone where the integrated dose value reaches the target value. In response to the beam OFF signal, as described above, the beam ON/OFF switch 11 is opened to stop the supply of the ion beam to the relevant angle zone. Also, the ON/OFF signal generator 307 generates the beam ON signal for the angle zone where the integrated dose value does not yet reach the target value. In response to the beam ON signal, as described above, the beam ON/OFF switch 11 is closed to continue the supply of the ion beam to the relevant angle zone.

Figure 11:
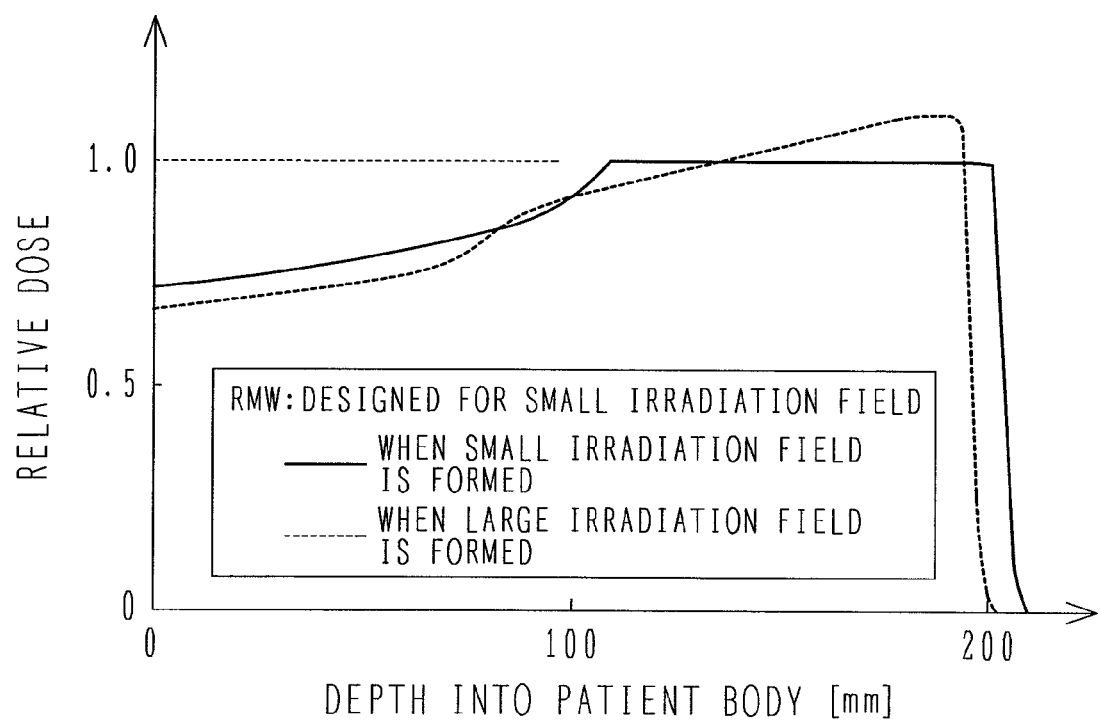
FIG. 11 is a graph showing a dose distribution in the direction of beam advance (direction of depth)

With reference to FIG. 11, one example in which a large irradiation field is formed using the RMW designed for a small irradiation field will be described below, in particular, regarding exemplary procedures and an effect upon the dose distribution in the direction of depth.

To enlarge the irradiation field of the RMW 202 designed for a small irradiation field, a spread of the incident ion beam in the perpendicular direction is increased. For example, by increasing the thickness of the first scatterer 206, the scattering rate of the ion beam in the perpendicular direction is increased and therefore the ion beam is spread out. With the spreading-out of the ion beam, however, the energy loss of the ion beam is also increased and the range of the ion beam is reduced. As another example, the ion beam may be spread out by moving the first scatterer 206 or the RMW 202 to a more upstream position along the path of the ion beam, thus increasing the distance through which the ion beam flies after the scattering. When the RMW 202 is arranged at a more upstream position along the path of the ion beam, the range of the ion beam is not changed, but a longer flying length of the ion beam is required. This results in an increase in size of the irradiation apparatus 200. Further, the ion beam entering the second scatterer 208 is enlarged. Uniformity of the ion beam in the perpendicular direction has to be obtained by correspondingly changing the second scatterer 208. Thus, since the material through which the ion beam passes is changed, the range of the ion beam and the shape of the Bragg curve are also changed. Consequently, the dose distribution in the direction of depth is changed as indicated by a dotted line in FIG. 11.

Figure 12:
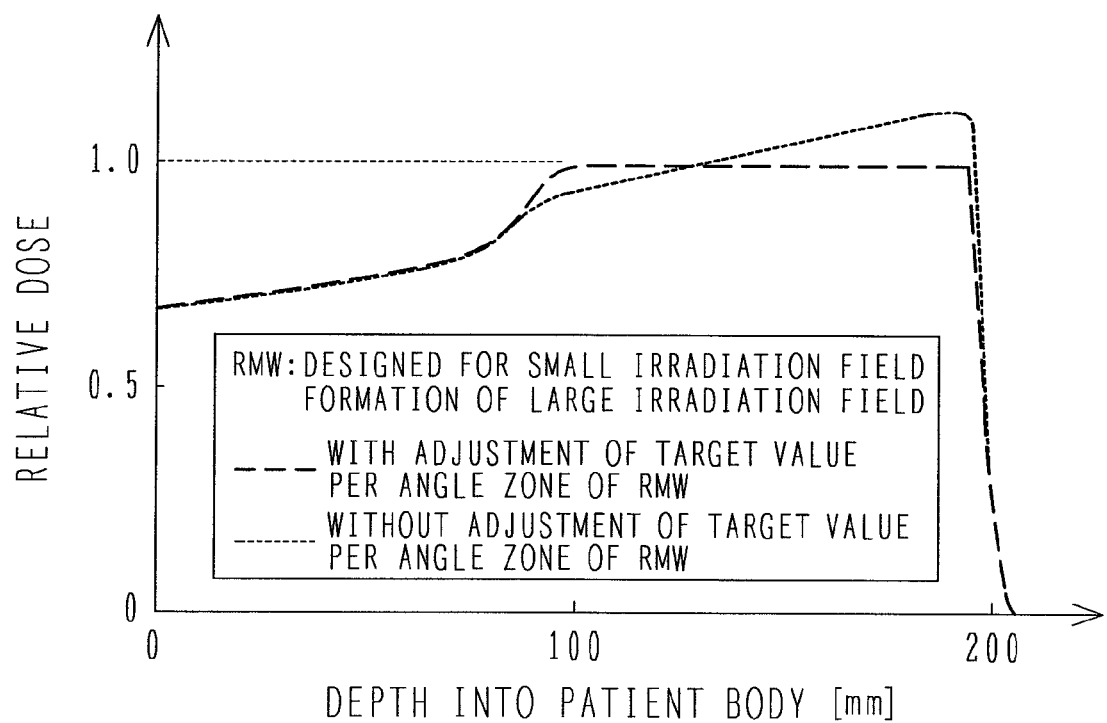
FIG. 12 is a graph showing a dose distribution in the direction of beam advance (direction of depth).

This embodiment is designed, as described above, to stop the supply of the ion beam to one(s) of the plural angle zones where the target value is attained, and to continue the supply of the ion beam to the other angle zone(s) where the target value is not yet attained. Accordingly, even when the dose distribution in the direction of depth is changed as a result of using the RMW 202 designed for the small irradiation field, it is possible to form a desired dose distribution (e.g., a uniform dose distribution) indicated by a broken line in FIG. 12. Stated another way, by properly setting the target value per angle zone of the RMW 202, the target value can be set depending on various positions in the direction of depth as seen from the above description. Because resulting dose changes can be calculated, the target value is just required to be set so that the desired dose distribution (e.g., the uniform dose distribution) can be obtained. Thus, by setting the target value in the memory 306 so as to provide the optimum dose distribution in the direction of depth, which is changed depending on the incident energy of the ion beam, the size of the irradiation field, the installed devices, etc., the number of the irradiation fields formable by one RMW 202 can be increased.

With the particle beam therapy system constructed as described above, the beam dose per angle zone can be changed while using one RMW 202, and therefore a variety of irradiation fields can be formed.

According to this embodiment, since a plurality of dose distributions can be formed using one RMW for plural levels of energy of the ion beam and various irradiation fields, the total number of RMWs used in treatments can be reduced. It is therefore possible to greatly reduce the number of times at which the RMW 202 has to be replaced because of differences in beam energy and size of the irradiation field, and to increase the number of patients who can be treated per year.

According to this embodiment, since the start and the stop of extraction of the ion beam (beam ON/OFF) are controlled such that the ion beam is not supplied to the angle zone of the RMW 202 where the target value is attained, while the ion beam is continuously supplied to the angle zone where the target value is not yet attained, the beam dose can be easily adjusted at various positions within the affected part 216a in the direction of advance of the ion beam. Such easy adjustment greatly reduces the probability of erroneous irradiation that the beam dose becomes excessive or deficient at various positions within the affected part 216a in the direction of advance of the ion beam. Further, the dose distribution within the affected part 216a in the direction of advance of the ion beam can be easily matched with the desired dose distribution decided in the treatment planning stage. This embodiment enables the probability of erroneous irradiation to be reduced to 0.

According to this embodiment, since the ion beam is not supplied to the angle zone of the RMW 202 where the target value is attained, while the ion beam is continuously supplied to the angle zone where the target value is not yet attained, the number of RMWs can be further reduced beyond the number that can be reduced with the above-described first function of the extracted beam amount controller.

According to this embodiment, the amount of the ion beam extracted from the synchrotron 5 (i.e., the extracted beam intensity) is controlled depending on the rotational angle of the RWM 202. Therefore, the ion beam intensity can be controlled depending on the magnitude of the target dose value per angle zone, and the irradiation can be progressed with higher efficiency. In addition, with the feature that the amount of the ion beam extracted from the synchrotron 5 is controlled depending on the rotational angle of the RWM 202, even when the required level of beam energy is changed with change from one patient to another, the RMW 202 used for the previous patent can also be used to form the desired dose distribution) within the affected part 216a in the direction of advance of the ion beam.

This embodiment includes the interlock signal generator 310, i.e., means for, during the irradiation of the ion beam, comparing the integrated dose of the irradiated ion beam with the target integrated dose of the ion beam in an angle zone group containing at least one of the plural angle zones of the RMW, and stopping the irradiation of the ion beam when, in any of the angle zones, the ion beam is irradiated in dose over the target value for the relevant angle zone. Therefore, if unexpected irradiation of the ion beam, e.g., excess irradiation over the target value, is detected as a result of successively comparing the integrated dose of the irradiated ion beam with the target dose of the ion beam during the irradiation of the ion beam, the irradiation of the ion beam can be stopped at once and higher reliability can be ensured.

Further, this embodiment includes means for stopping the irradiation of the ion beam when a ratio of the dose of the ion beam irradiated to a first angle zone group, which contains at least one of the plural angle zones of the RMW, to the dose of the ion beam irradiated to a second angle zone group, which contains at least one of the angle zones not contained in the first angle zone group, exceeds a preset range of value. Therefore, if excess irradiation of the ion beam over the preset allowable value is detected as a result of successively comparing the ratio in the integrated dose of the irradiated ion beam between the first angle zone group and the second angle zone group with a ratio in the target dose of the ion beam between both the groups during the irradiation of the ion beam, the irradiation of the ion beam can be stopped at once and higher reliability can be ensured.

While this embodiment has been described, by way of example, as using the synchrotron 5 as the circular accelerator, the present invention can also be practiced using a cyclotron instead of the synchrotron 5. In the case of the cyclotron, the start and the stop of extraction of the ion beam from the cyclotron to the irradiation apparatus can be controlled by turning on/off a power supply for an ion source from which an ion beam is supplied to the cyclotron. A particle beam therapy system using the cyclotron as the circular accelerator is constructed such that the synchrotron 5 in the particle beam therapy system, shown in FIG. 1, is replaced with the cyclotron and the RF supply unit 18 is omitted. In the particle beam therapy system using the cyclotron, the beam ON signal and the beam OFF signal both outputted from the ON/OFF signal generator 307 are used to perform ON/OFF control of a switch (ON/OFF device) disposed in a line connecting the power supply and the ion source. With the control of such a switch, as in the embodiment of FIG. 1, the ion beam can be supplied to the angle zone of the RMW 202 where the target value is not yet attained while stopping the supply of the ion beam to the angle zone where the target value is attained. It is hence possible to easily adjust the beam doses at various positions within the affected part 216*a* in the direction of advance of the ion beam, and to greatly reduce the probability of erroneous irradiation that the beam dose becomes excessive or deficient at the various positions within the affected part 216*a* in the direction of advance of the ion beam.

What is claimed is:

1. A charged particle beam irradiation system comprising:
    an accelerator for accelerating a charged particle beam to be extracted;
    an energy adjusting device through which the charged particle beam extracted from said accelerator passes; and
    a beam irradiation device for irradiating the charged particle beam having passed through said energy adjusting device to an irradiation target,
    wherein said energy adjusting device is rotatable and has different axial thicknesses in a rotating direction thereof; and
    said charged particle beam irradiation system further comprises a control unit for controlling starting and stopping of extraction of the charged particle beam from said accelerator in accordance with a rotational angle of said energy adjusting device and a dose of the charged particle beam having passed through said energy adjusting device.

2. The charged particle beam irradiation system according to claim 1, wherein said control unit determines integrated values of the dose of the charged particle beam having passed through a plurality of zones of said energy adjusting device, which are divided in the rotating direction, based on the rotational angle of said energy adjusting device and the dose of the charged particle beam having passed through said energy adjusting device, and controls starting and stopping of extraction of the charged particle beam from said accelerator in accordance with the integrated value per zone.

3. The charged particle beam irradiation system according to claim 1, further comprising:
    an angle detector for detecting the rotational angle of said energy adjusting device; and
    a measuring unit for measuring the dose of the charged particle beam having passed through said energy adjusting device,
    wherein said control unit controls starting and stopping of extraction of the charged particle beam from said accelerator in accordance with the detected rotational angle and the measured dose.

4. The charged particle beam irradiation system according to claim 2, wherein said control unit stops the extraction of the charged particle beam from said accelerator when a zone in which the integrated value of the dose of the charged particle beam reaches a target dose is positioned in a beam path, and allows the extraction of the charged particle beam from said accelerator when a zone in which the integrated value of the dose of the charged particle beam does not yet reach the target dose is positioned in the beam path.

5. The charged particle beam irradiation system according to claim 2, further comprising a safety device for stopping the extraction of the charged particle beam from said accelerator when the integrated value of the dose of the charged particle beam in any of the zones exceeds an allowable value set for the relevant zone.

6. The charged particle beam irradiation system according to claim 2, further comprising a safety device for stopping the extraction of the charged particle beam from said accelerator when a ratio of the integrated value of the dose of the charged particle beam having passed through a first angle zone of said energy adjusting device in the rotating direction to the integrated value of the dose of the charged particle beam having passed through a second angle zone, which differs from said first angle zone, exceeds a preset allowable value.

7. The charged particle beam irradiation system according to claim 2, further comprising a display for displaying the integrated value of the dose of the charged particle beam per zone.

8. A charged particle beam irradiation system comprising:
    an accelerator for accelerating a charged particle beam to be extracted, said accelerator including an RF knockout unit for beam extraction;
    an energy adjusting device through which the charged particle beam extracted from said accelerator passes; and
    a beam irradiation device for irradiating the charged particle beam to an irradiation target,
    wherein said energy adjusting device is rotatable and has different axial thicknesses in a rotating direction thereof; and
    said charged particle beam irradiation system further comprises a control unit for controlling starting and stopping of an RF signal applied to said RF knockout unit in accordance with a rotational angle of said energy adjusting device and a dose of the charged particle beam having passed through said energy adjusting device.

9. A charged particle beam irradiation system comprising:
    an ion source for generating a charged particle beam;
    an accelerator for accelerating the charged particle beam emitted from said ion source; and
    a beam irradiation device for irradiating the charged particle beam to an irradiation target, said beam irradiation device including an energy adjusting device through which the charged particle beam extracted from said accelerator passes;
    wherein said energy adjusting device is rotatable and has different axial thicknesses in a rotating direction thereof; and
    said charged particle beam irradiation system further comprises a control unit for controlling starting and stopping of extraction of the charged particle beam from said ion source in accordance with a rotational angle of said energy adjusting device and a dose of the charged particle beam having passed through said energy adjusting device.

10. A charged particle beam irradiation system comprising:
    an accelerator for accelerating the charged particle beam to be extracted; and
    a beam irradiation device including an energy adjusting device through which the charged particle beam extracted from said accelerator passes, and irradiating the charged particle beam having passed through said energy adjusting device to an irradiation target, wherein said energy adjusting device is rotatable and has different axial thicknesses in a rotating direction thereof; and said charged particle beam irradiation system further comprises a control unit for stopping supply of the charged particle beam to one or more of a plurality of zones in each of which a target dose is attained, said zones being formed by dividing said energy adjusting device in the rotating direction, and for allowing the supply of the charged particle beam to one or more other zones in each of which a target dose is not yet attained.

11. The charged particle beam irradiation system according to claim 10, wherein said control unit stops the supply of the charged particle beam to one or more zones in each of which an integrated value of dose of the charged particle beam having passed through the relevant zone reaches a target dose, and allows the supply of the charged particle beam to one or more other zones in each of which the integrated value of dose of the charged particle beam does not yet reach a target dose.

12. The charged particle beam irradiation system according to claim 10, further comprising an angle detector for detecting a rotational angle of said energy adjusting device, wherein said control unit allows and stops the supply of the charged particle beam in accordance with the detected rotational angle.

13. A charged particle beam extraction method comprising the steps of:
supplying a charged particle beam extracted from an accelerator to an energy adjusting device which is rotatable and has different axial thicknesses in a rotating direction thereof; and
controlling starting and stopping of extraction of the charged particle beam from said accelerator in accordance with a rotational angle of said energy adjusting device and a dose of the charged particle beam having passed through said energy adjusting device.

14. A charged particle beam extraction method comprising the steps of:
supplying a charged particle beam extracted from an accelerator to an energy adjusting device which is rotatable and has different axial thicknesses in a rotating direction thereof; and
stopping supply of the charged particle beam to one or more of a plurality of zones in each of which a target dose is attained, said zones being formed by dividing said energy adjusting device in the rotating direction, and allowing the supply of the charged particle beam to one or more other zones in each of which a target dose is not yet attained.

* * * * *